United States Patent
Govea

(10) Patent No.: US 9,375,563 B2
(45) Date of Patent: Jun. 28, 2016

(54) SYSTEMS AND METHODS OF FORMING CONTACT ASSEMBLIES FOR LEADS OF ELECTRICAL STIMULATION SYSTEMS

(71) Applicant: BOSTON SCIENTIFIC NEUROMODULATION CORPORATION, Valencia, CA (US)

(72) Inventor: Michael Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 8 days.

(21) Appl. No.: 14/096,713

(22) Filed: Dec. 4, 2013

(65) Prior Publication Data

US 2014/0163656 A1 Jun. 12, 2014

Related U.S. Application Data

(60) Provisional application No. 61/734,233, filed on Dec. 6, 2012.

(51) Int. Cl.
*A61N 1/05* (2006.01)
*H01R 43/02* (2006.01)
*H01R 43/24* (2006.01)
(Continued)

(52) U.S. Cl.
CPC ............... *A61N 1/05* (2013.01); *A61N 1/0551* (2013.01); *H01R 9/03* (2013.01); *H01R 9/11* (2013.01); *H01R 43/02* (2013.01); *H01R 43/24* (2013.01); *H01R 2201/12* (2013.01); *Y10T 29/49176* (2015.01); *Y10T 29/49179* (2015.01)

(58) Field of Classification Search
CPC ......... A61N 1/05; A61N 1/0551; H01R 9/11; H01R 9/03; H01R 43/02; H01R 43/24; H01R 2201/12; Y10T 29/49176; Y10T 29/49179
See application file for complete search history.

(56) References Cited

U.S. PATENT DOCUMENTS 6,181,969 B1 1/2001 Gord
6,216,045 B1 * 4/2001 Black et al. ................... 607/122
(Continued)

FOREIGN PATENT DOCUMENTS

WO 2012087416 A1 6/2012

OTHER PUBLICATIONS

International Search Report and Written Opinion for PCT/US2013/073122 mailed Feb. 19, 2014.

*Primary Examiner* — Peter DungBa Vo
*Assistant Examiner* — Jeffrey T Carley
(74) *Attorney, Agent, or Firm* — Lowe Graham Jones PLLC; Bruce E. Black

(57) ABSTRACT

A method of forming an electrical stimulation lead includes molding an electrically-nonconductive substrate over and between spaced-apart electrically-conductive contacts to form a multi-contact lead assembly. The contacts are disposed along a first face of the substrate with a first face of each of the contacts exposed along the first face of the substrate and an opposing second face of each of the contacts covered by material forming a second face of the substrate. The multi-contact lead assembly is coupled along a first end portion of a lead body with the first face of the multi-contact lead assembly conforming to a shape of an outer surface of the lead body, and with the multi-contact lead assembly wrapping around the outer surface of the lead body. Conductors extending along a length of the lead body are electrically coupled to each of the contacts of the multi-contact lead assembly.

20 Claims, 9 Drawing Sheets

(51) Int. Cl.
*H01R 9/11* (2006.01)
*H01R 9/03* (2006.01)

(56) References Cited

U.S. PATENT DOCUMENTS

| | | |
|---|---|---|
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2004/0186542 A1* | 9/2004 | van Venrooij ........ A61N 1/0529 607/116 |
| 2007/0150036 A1 | 6/2007 | Anderson |
| 2008/0015668 A1* | 1/2008 | Soukup .................... A61N 1/05 607/115 |
| 2010/0070009 A1* | 3/2010 | Barker .................... A61N 1/05 607/117 |
| 2010/0256694 A1* | 10/2010 | Barker .................... A61N 1/05 607/2 |
| 2012/0197375 A1 | 8/2012 | Pianca et al. |

* cited by examiner

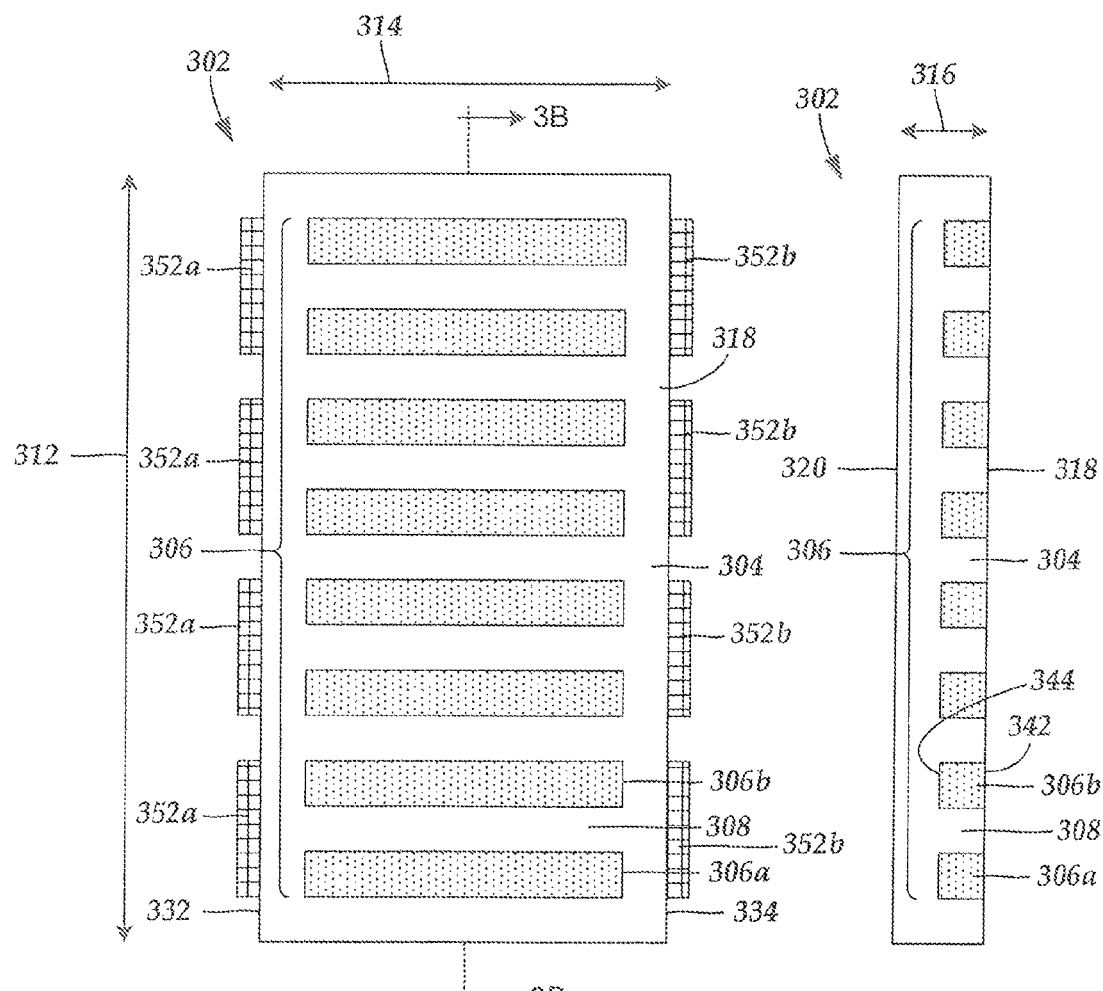

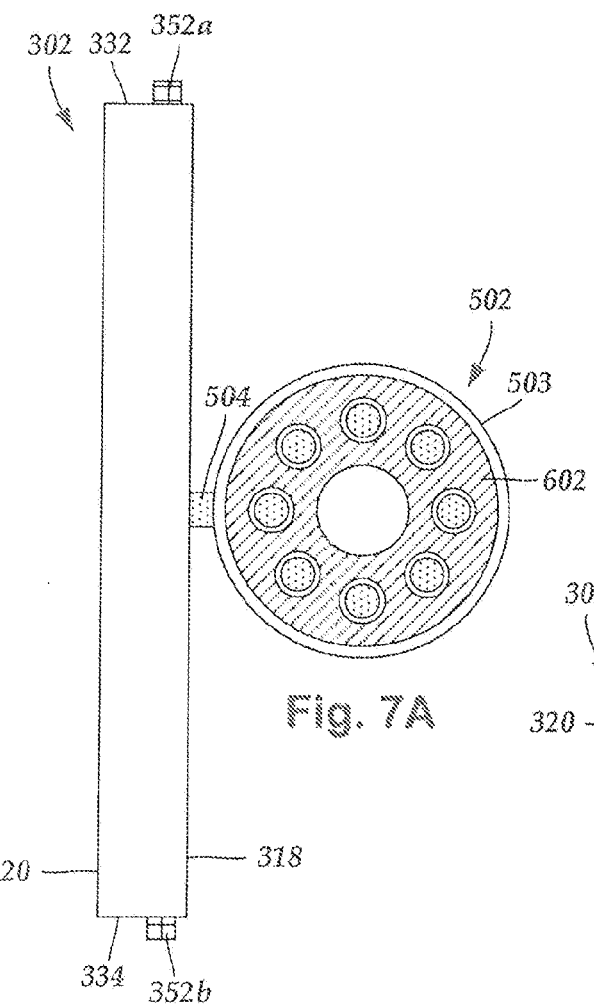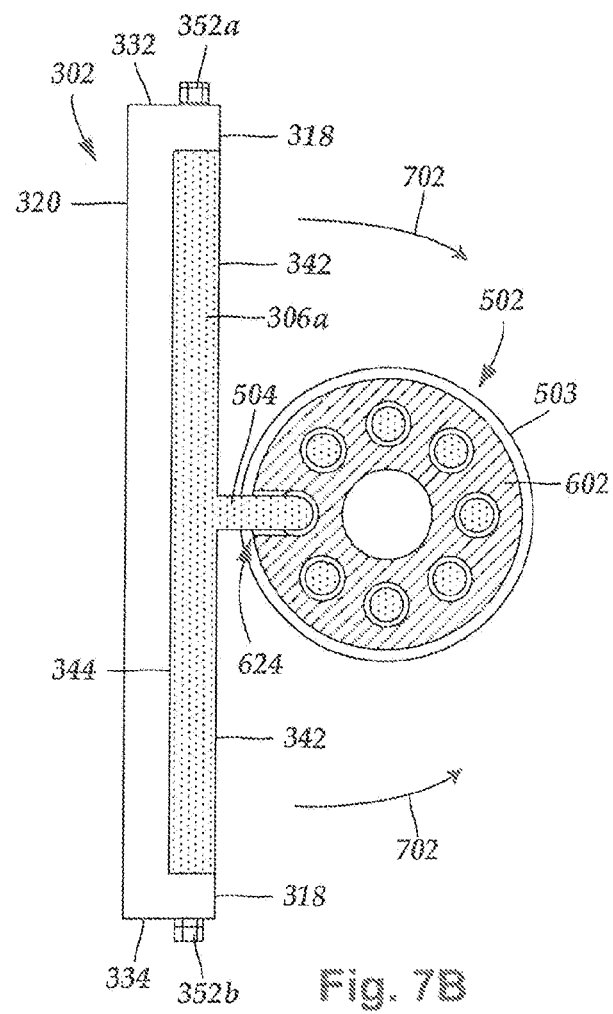

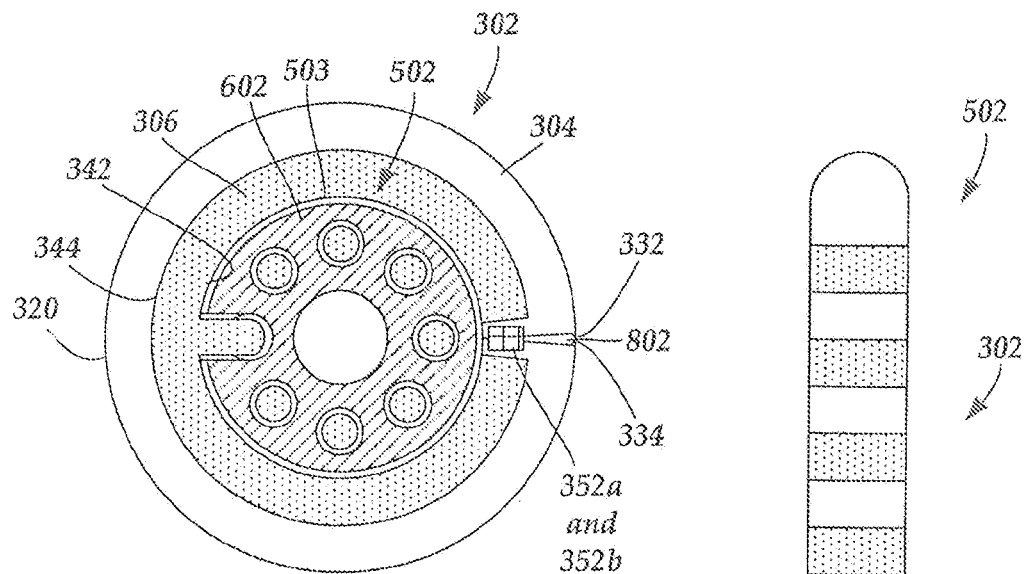
Fig. 8A
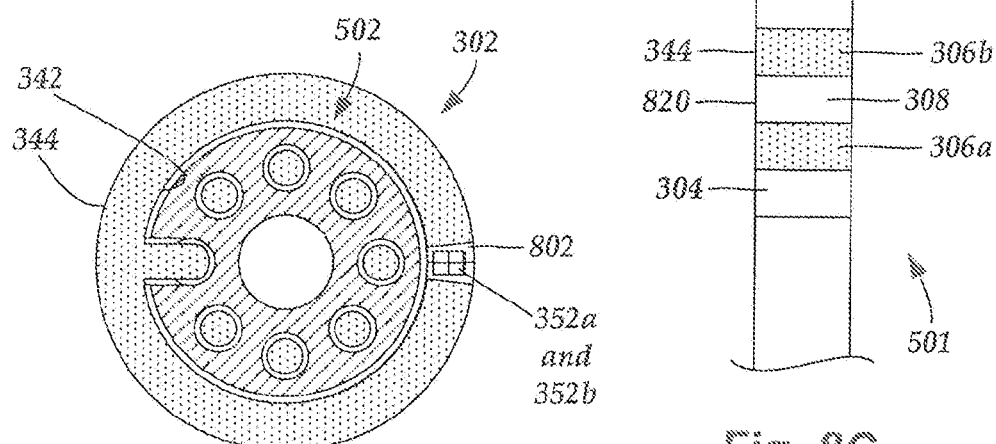
Fig. 8B
Fig. 8C

SYSTEMS AND METHODS OF FORMING CONTACT ASSEMBLIES FOR LEADS OF ELECTRICAL STIMULATION SYSTEMS

CROSS-REFERENCE TO RELATED APPLICATIONS

This application claims the benefit under 35 U.S.C. §119 (e) of U.S. Provisional Patent Application Ser. No. 61/734,233 filed Dec. 6, 2012, which is incorporated herein by reference.

FIELD

The present invention is directed to the area of implantable electrical stimulation systems and methods of making and using the systems. The present invention is also directed implantable electrical stimulation leads having contacts formed on multi-contact assemblies, as well as methods of making and using the leads, contacts, contact assemblies, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a method of forming an electrical stimulation lead includes molding an electrically-nonconductive substrate over and between multiple spaced-apart electrically-conductive contacts to form a multi-contact lead assembly having multiple contacts disposed along a substrate. The substrate has a first face and an opposing second face. The contacts each have a first face and an opposing second face. The contacts are disposed along the first face of the substrate with the first face of each of the contacts exposed along the first face of the substrate and the opposing second face of each of the contacts covered by material forming the second face of the substrate. The contacts include a first contact and a second contact. The multi-contact lead assembly is coupled along a first end portion of a lead body with the first face of the multi-contact lead assembly conforming to a shape of an outer surface of the lead body with the multi-contact lead assembly wrapping around the outer surface of the lead body. Individual conductors extending along a length of the lead body are electrically coupled to each of the contacts of the multi-contact lead assembly.

In another embodiment, an electrical stimulation lead assembly includes a lead body having a distal end portion, a proximal end portion, an outer surface, and a circumference. Multiple terminals are disposed along the proximal end portion of the lead body. A single-piece multi-contact assembly is disposed along the distal end portion of the lead body and is wrapped around the circumference of the lead body. The multi-contact assembly has a front face, a rear face opposite to the front face, a width, and a thickness. The rear face of the multi-contact assembly abuts the outer surface of the lead body. The multi-contact assembly includes multiple longitudinally-spaced-apart electrodes each extending across the entire thickness of the multi-contact assembly from the front face to the rear face. The electrodes include a first electrode and a second electrode. An electrically-nonconductive spacer is disposed between the first electrode and the second electrode and electrically isolates the first electrode from the second electrode. The spacer extends across the entire thickness of the multi-contact assembly from the front face to the rear face. The lead assembly further includes multiple conductors. Each of the multiple conductors electrically couples each of the terminals to at least one of the electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a schematic bottom view of one embodiment of a first side of multi-contact assembly that includes multiple contacts disposed in an electrically-nonconductive substrate, according to the invention;

FIG. 3B is a schematic cross-sectional side view of one embodiment of the multi-contact assembly of FIG. 3A, according to the invention;

FIG. 7A is a schematic transverse cross-sectional view of one embodiment of the lead body of FIG. 5 at a location proximal to where a conductor disposed within one of the conductor lumens of the multi-lumen conductor guide of FIG. 7A extends to the multi-contact assembly of FIG. 3A, according to the invention;

FIG. 7B is a schematic transverse cross-sectional view of one embodiment of the lead body of FIG. 5 at a location where a conductor disposed within a conductor lumen of the multi-lumen conductor guide of FIG. 6A electrically couples to a contact of the multi-contact assembly of FIG. 3A, according to the invention;

FIG. 8A is a schematic transverse cross-sectional view of one embodiment of the multi-contact assembly of FIG. 7B disposed over the lead body of FIG. 7B, where the multi-contact assembly is wrapped around an outer surface of the lead body such that rear faces of contacts and a rear face of the substrate of the multi-contact assembly abut the lead body and opposing front faces of the contacts are buried beneath a front face of the substrate, according to the invention;

FIG. 8B is a schematic transverse cross-sectional view of one embodiment of the multi-contact assembly of FIG. 8A disposed over the lead body of FIG. 8A, where opposing ends of the multi-contact assembly have been coupled together, and where a front face of a substrate of the multi-contact assembly has been ground down to expose front faces of electrodes of the multi-contact assembly, according to the invention;

FIG. 8C is a schematic side view of one embodiment of a distal portion of the lead body of FIG. 8B with the multi-contact assembly of FIG. 8B disposed over the lead body of FIG. 8B, according to the invention.

DETAILED DESCRIPTION

The present invention is directed to the area of implantable electrical stimulation systems and methods of making and using the systems. The present invention is also directed to implantable electrical stimulation leads having contacts formed on multi-contact assemblies, as well as methods of making and using the leads, contacts, contact assemblies, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
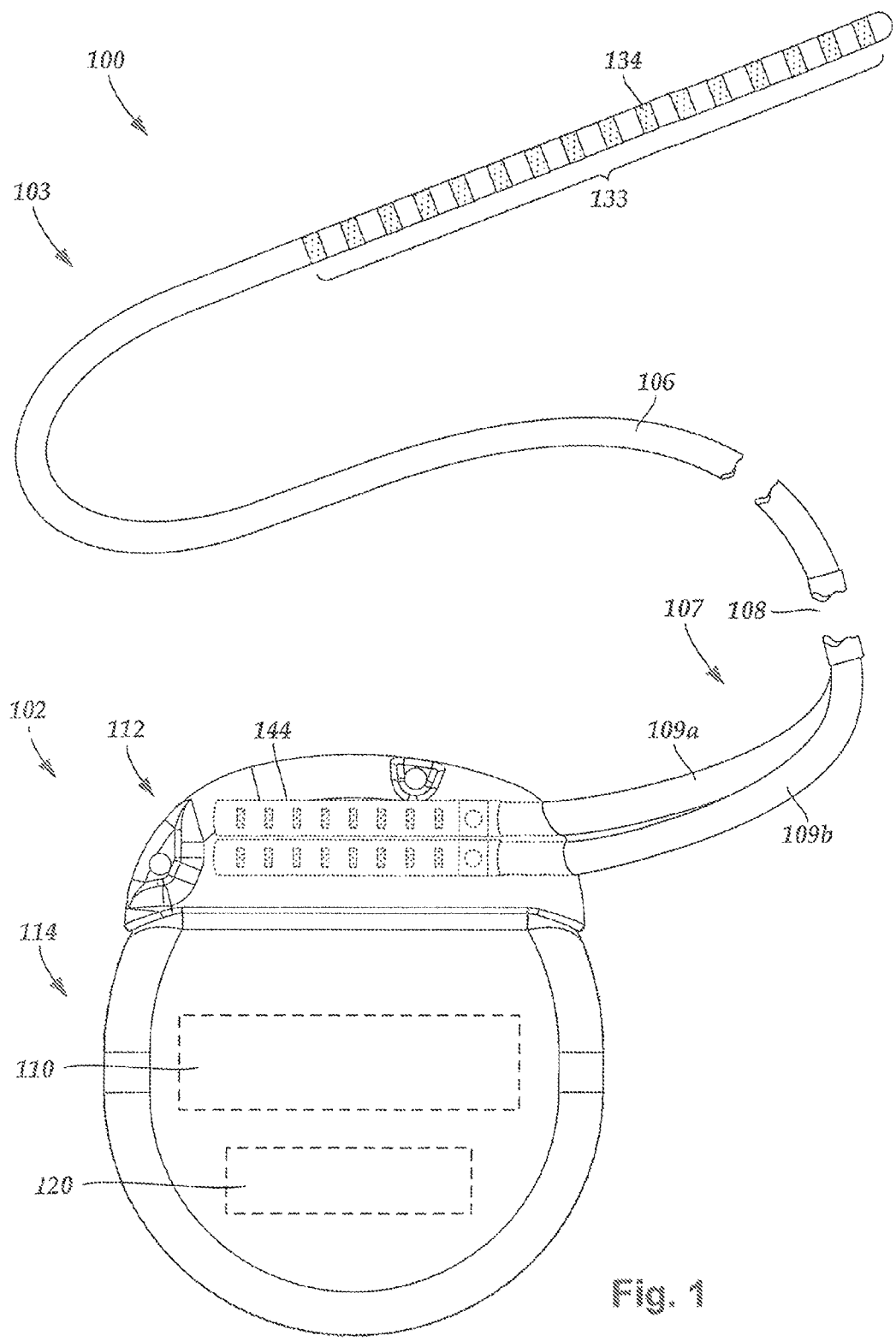
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
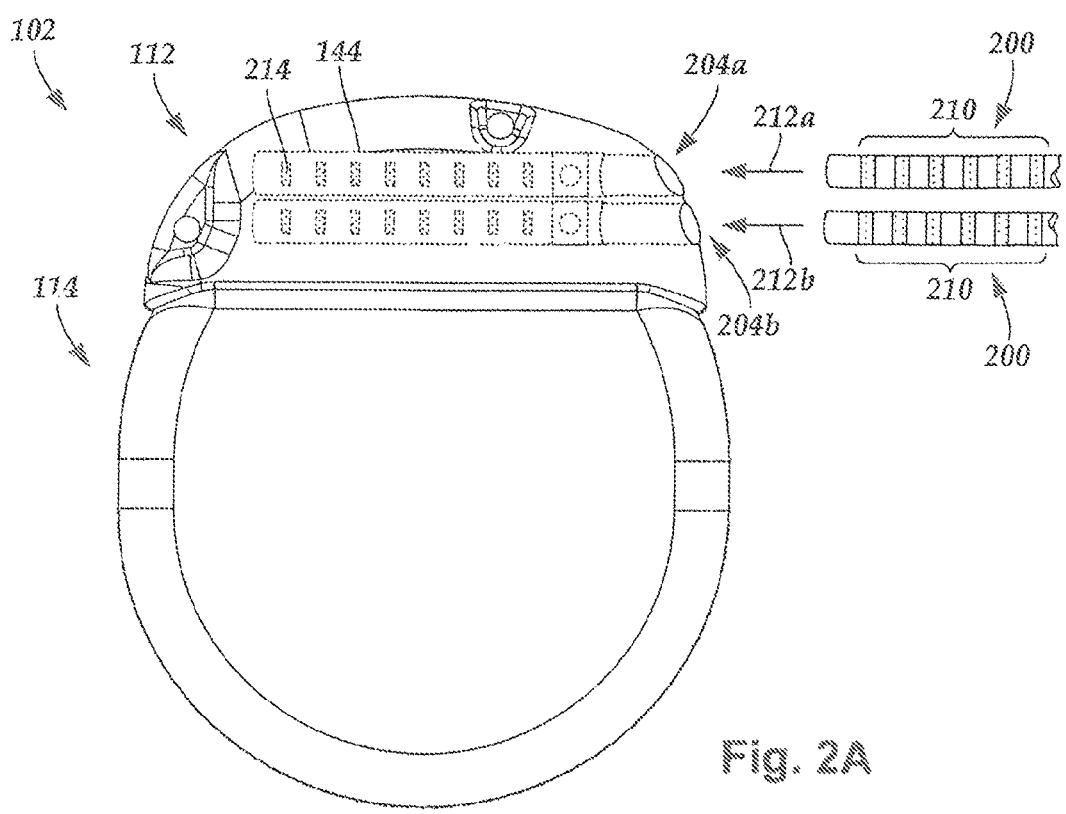
FIG. 2A is a schematic view of one embodiment of the control module of FIG. 1 configured and arranged to electrically couple to an elongated device, according to the invention.
Figure 2B:
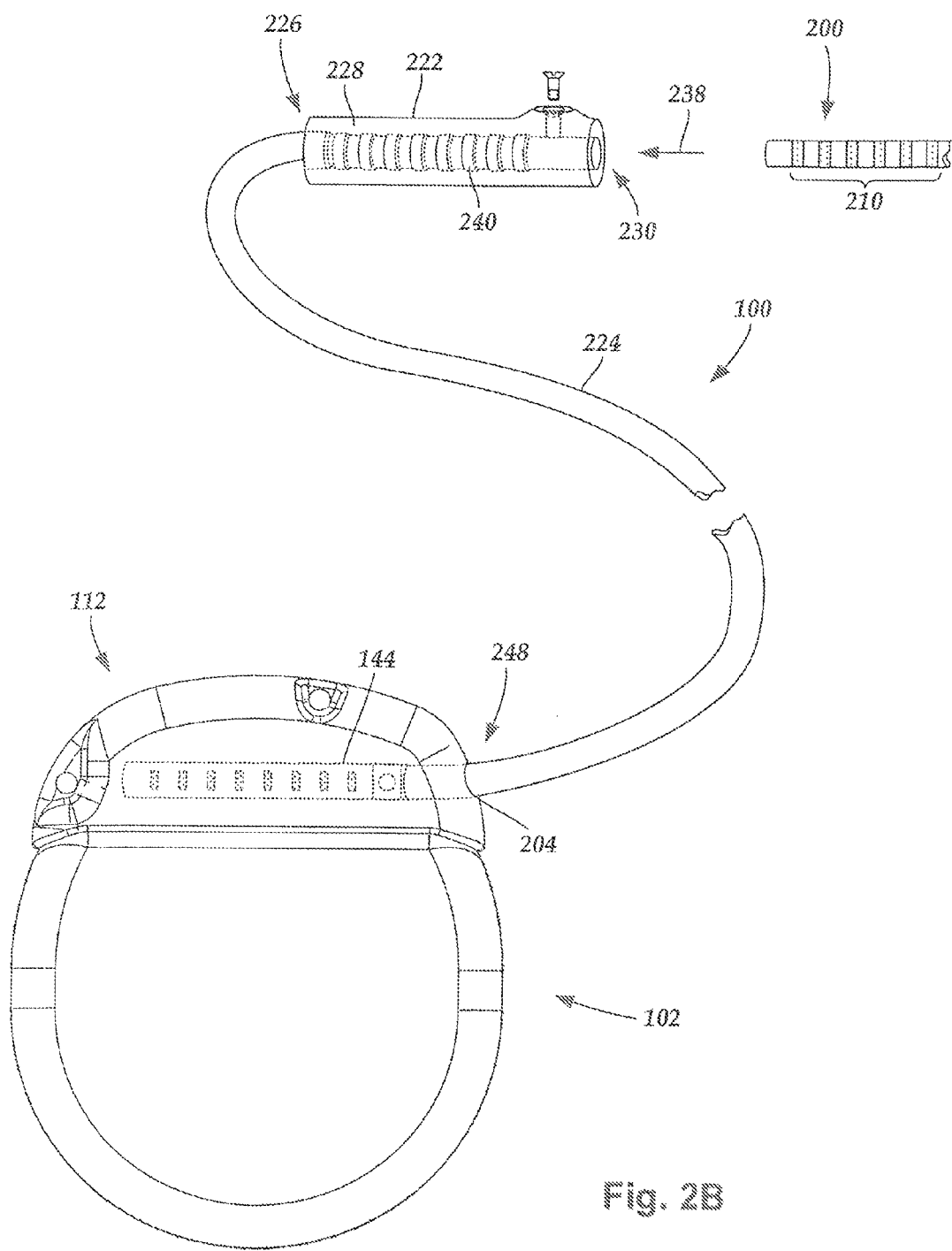
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Conductor wires (not shown) extend from the terminals to the electrodes 134. Typically, one or more electrodes 134 are electrically coupled to each terminal. In at least some embodiments, each terminal is only connected to one electrode 134.

The conductor wires ("conductors") may be embedded in the non-conductive material of the lead body 106 or can be disposed in one or more lumens (606 in FIG. 6A) extending along the lead body 106. In some embodiments, there is an individual lumen for each conductor. In other embodiments, two or more conductors may extend through a lumen. There may also be one or more lumens (608 in FIG. 6A) that open at, or near, the proximal end of the lead body 106, for example, for inserting a stylet to facilitate placement of the lead body 106 within a body of a patient. Additionally, there may also be one or more lumens (not shown) that open at, or near, the distal end of the lead body 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Turning to FIG. 3A, at least some conventional leads form contact assemblies by sliding electrically-conductive contacts (e.g., terminals and electrodes) onto end portions of the lead body with electrically-nonconductive spacers disposed between adjacent contacts. The contacts and spacers are typically coupled to one another by reflowing, one or more adhesives, or the like. Forming such contact assemblies may be labor-intensive and provide inconsistent contact pitches (i.e., distances between centers of adjacent contacts). Additionally, forming leads using such techniques may involve blind welding lead conductors to the contacts. Blind welding conductors to contacts may also be labor-intensive and, additionally, may provide inconsistent electrical connections.

As herein described, a lead includes a multi-contact assembly disposed along an end portion of a lead body. The multi-contact assembly includes multiple contacts disposed on a substrate. In at least some embodiments, the multiple contacts are disposed on a single substrate. In at least some embodiments, the multi-contact assembly is molded. The multi-contact assembly may be attached to either end portion of the lead body. For instance, in at least some embodiments the multi-contact assembly is configured to couple to a distal end portion of the lead body and includes electrodes as the contacts. In at least some other embodiments, the multi-contact assembly is configured to couple to a proximal portion of the lead body and includes terminals as the contacts.

FIG. 3A is a schematic bottom view of one embodiment of a multi-contact assembly 302 that includes a flexible, electrically-nonconductive substrate 304 ("substrate") and multiple contacts 306 (e.g., terminals or electrodes) disposed along the substrate 304. FIG. 3B is a side view of the substrate 304 and the contacts 306 of the multi-contact assembly 302. The substrate 304 has a length 312, a width 314, a thickness 316, a first face 318, an opposing pre-second face 320, a first side 332, and an opposing second side 334. In at least some embodiments, the substrate 304 is manufactured as a single-piece structure.

FIGS. 3A-3B show eight contacts 306 disposed on the substrate 304. It will be understood that any suitable number of contacts 306 may be disposed along the substrate 304 including, for example, one, two, three, four, five, six, seven, eight, nine, ten, eleven, twelve, fourteen, sixteen, twenty, twenty-four, twenty-eight, thirty-two, or more contacts 306. As will be recognized, other numbers of contacts 306 may also be used.

In some embodiments, at least one of the contacts 306 extends across the entire width 312 of the substrate 304. In at least some embodiments, at least one of the contacts 306 extends across substantially the entire width 312 of the substrate 304. In at least some embodiments, two or more contacts 306 extend across the width 312 of the substrate 304.

In the illustrated embodiment, the contacts 306 are disposed along the first face 318 of the substrate 304. Each contact 306 is electrically-isolated from one another in a spaced-apart arrangement with a spacer portion 308 of the substrate 304 disposed between adjacent contacts 306. For example, as shown in FIGS. 3A-3B, the contacts 306 includes a first contact 306a and a second contact 306b, where the first and second contacts 306a and 306b are separated from one another by the spacer portion 308 of the substrate 304. In at least some embodiments, the spacer portions 308 of the substrate 304 are formed from the same material as the remaining portions of the substrate 304.

The spacer portions 308 of the substrate 304 have lengths (along the length 312 dimension of the substrate 304) sufficient to prevent, or at least reduce, undesired electrical interactions between adjacent contacts 306. In at least some embodiments, the spacer portions 308 have equal lengths. It may be advantageous to have a consistent spacing between adjacent contacts; however, the spacing may vary in certain instances. The varying spacing between the adjacent contacts 306 can be dictated by various factors. Exemplary factors may include: 1) positioning of contacts 306 selected to reduce stimulation thresholds for specific nerves and/or tissues, 2) positioning of contacts 306 directed towards affording flexibility in a choice of contact spacing, and so forth.

Optionally, the multi-contact assembly 302 includes one or more first interlocking features 352a disposed along the first side 332 of the substrate 304, and one or more second interlocking features 352b disposed along the second side 334 of the substrate 304. In at least some embodiments, the second interlocking features 352b are configured and arranged to couple to corresponding first interlocking features 352a when the substrate 304 is formed into a cylinder. It will be understood that the two interlocking features (352a and 352b) may be coupled together when the substrate 304 is formed into other shapes including, for example, rectangular, triangular, or any other shapes, depending on the underlying lead (as discussed in more detail below).

FIGS. 3A-3B show four second interlocking features 352b and four corresponding first interlocking features 352a. It will be understood that any suitable number of interlocking features 352a and 352b may be disposed along the substrate 304 including, for example, one, two, three, four, five, six, seven, eight, nine, ten, eleven, twelve, fourteen, sixteen, twenty, or more interlocking features 352a and 352b. As will be recognized, other numbers of interlocking features 352a and 352b may also be used.

Any suitable type of interlocking features 352a and 352b may be disposed along the substrate 304 (e.g., hooks and loops, snaps, clips, or the like). Other suitable mechanisms to couple the opposing ends (332 and 334) of the substrate 304 may include, for example, one or more adhesives, or the like. Further details of coupling opposing ends (332 and 334) of the substrate 304 to one another around a portion of a lead will be described in detail below, with reference to FIGS. 8A-8B.

The contacts 306 each include a first face 342 and an opposing second face 344. The first faces 342 of the contacts 306 are disposed along the first face 318 of the substrate 304, while the second faces 344 of the contacts 306 are buried within the substrate 304. The first faces 342 of the contacts may be either inset from, flush with, or raised from the first face 318 of the substrate 304. As discussed in more detail below with reference to FIG. 8C, the second faces 344 of the contacts 306 may subsequently be exposed by grinding down the pre-second face 320 of the substrate 304.

In some embodiments, the thickness 316 of the substrate 304 depends on the desired flexibility of the contact assembly 302. In at least some embodiments, the flexibility of the contact assembly 302 has an inverse relation with the thickness 316 of the substrate 304. It will be understood that the thickness 316 of the non-conductive substrate 304 may depend on other suitable factors including, for example, the thickness of the contacts 306 to be embedded within the substrate 304, or the like.

Figure 4A:
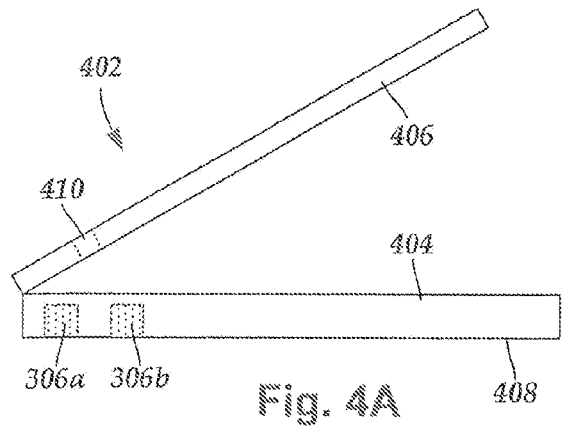
FIG. 4A is a schematic side view of one embodiment of two of the contacts of FIG. 3A disposed in a mold with the two contacts spaced apart from one another along a bottom surface of the mold, according to the invention.

Turning to FIG. 4A, the multi-contact assembly 302 may be fabricated in any suitable manner. In at least some embodiments, the contacts 306 are disposed in spaced-apart wells formed along a non-conductive base (i.e., the substrate 304). In at least some embodiments, the substrate is injection molded around the contacts, with the contacts arranged in a mold in a desired pitch (i.e., distances between centers of adjacent contacts), thereby enabling non-conductive material to be disposed between and below the contacts.

Figure 4B:
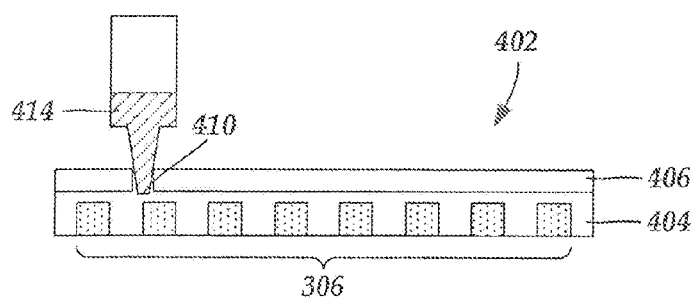
FIG. 4B is a schematic cross-sectional view of one embodiment of each of the contacts of FIG. 3A disposed in the mold of FIG. 4A, with the contacts each spaced apart from one another, and with material forming the non-conductive substrate of the multi-contact assembly being input to the mold via an injection mold, according to the invention.

When using an injection molding technique, the contacts 306 may be placed within a mold 402 at a desired pitch, as shown in FIGS. 4A-4B. In FIG. 4A, a first contact 306a and a second contact 306b are shown disposed along a bottom surface 408 of a bottom portion 408 in the mold 402. The mold 402 defines an injection port 410 for injecting the material of the substrate 406 into the bottom portion 408 of the mold 402. Optionally, the mold 406 includes a top portion 406 that may be disposed over the bottom portion 408.

In FIG. 4B, each of the contacts 306 is shown disposed in the mold 402 and material 414 of the substrate 304 is being injected into the mold 402 through the injection port 410. In some embodiments, the bottom portion 404 of the mold 402 may define a number of slits or other mechanism (not shown) for holding the contacts 306 at particular positions. Such a mechanism may further ensure a particular pitch is obtained.

It will be understood that the shape and dimensions of the mold 402 may vary depending on the desired shape and dimensions of the contact assembly (302 in FIG. 3A). The material 414 is injected over and between the conductive contacts 306, which are disposed along the bottom surface 408 of the mold 402. Once the material 414 is cured within the mold 402, the molded product (i.e., the multi-contact assembly 302) is released from the mold 402.

In some embodiments, the material 414 includes any suitable electrically-nonconductive material including, but not limited to, polymers, composites, or the like. Examples may include silicone, polyurethane, or the like. In at least some embodiments, the material 414 is in a pre-solidified state before being injected in the bottom portion 404 of the mold 402. Thereafter, the material 414 may solidify at room temperature. Alternatively, the material 414 can also be heated before injection, and may be cooled using any conventional device or process to solidify the non-conductive material 414 within the mold 402.

Figure 5:
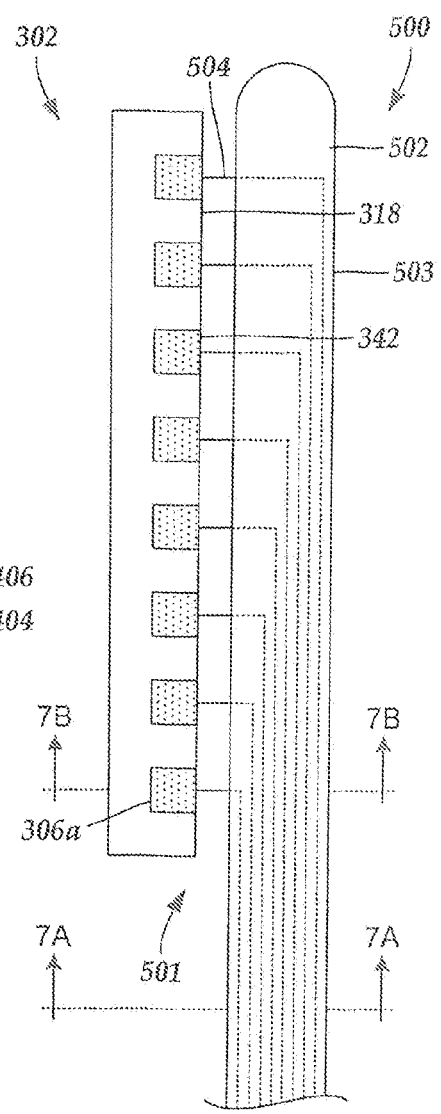
FIG. 5 is a schematic side view of one embodiment of contacts of the multi-contact assembly of FIG. 3B electrically coupled to conductors extending along a schematic transverse cross-sectional view of one embodiment of a distal portion of a lead body, according to the invention.

Turning to FIG. 5, once the multi-contact assembly is formed, the multi-contact assembly can be coupled to a lead. FIGS. 5-8C describe the multi-contact assembly being coupled to a distal end portion of a lead body. It will be understood that the multi-contact assembly can be coupled to either (or both) a distal end portion or a proximal end portion of a deep brain stimulation lead, or a percutaneous spinal cord stimulation lead, or the like. Additionally, the multi-contact assembly disclosed herein can be coupled, for example, along a proximal end portion of a paddle lead.

FIG. 5 shows the contact assembly 302 disposed in proximity to a distal end portion 501 of a lead body 502 of a lead 500. In FIG. 5, the contact assembly 302 is shown disposed in proximity to the lead 500 such that the first face 318 of the substrate 304 is disposed is adjacent to an outer surface 503 of the lead body 502. Conductors 504 extend along the lead body 502 with an end of each of the conductors 504 extending outwardly from the outer surface 503 of the lead 500 along the distal end portion 501 of the lead body 502.

In FIG. 5, the portions of the conductors 504 extending outwardly from the lead body 502 are shown coupled to first faces 342 of the contacts 306. In at least some embodiments, the opposing ends of the conductors 504 are coupled to, or coupleable to, contacts disposed along a proximal end portion of the lead body 502 (not shown). The conductors 504 can be electrically coupled to the contacts 306 in any suitable manner including, for example, welding, crimping, soldering, or the like.

Figure 6A:
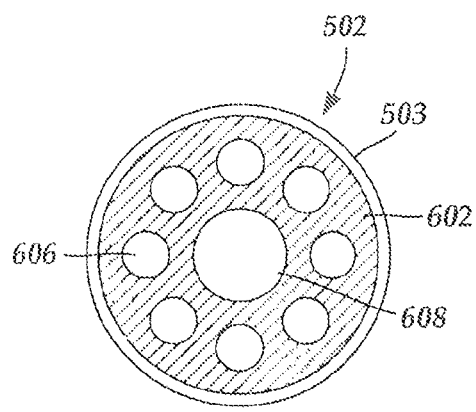
FIG. 6A is a schematic transverse cross-sectional view of one embodiment of a multi-lumen conductor guide of the lead body of FIG. 5, the multi-lumen conductor guide defining multiple conductor lumens, according to the invention.

Turning to FIG. 6A, the conductors 504 may be disposed along the lead body 502 in any suitable manner. In at least some embodiments, the conductors 504 may extend along the lead body 502 in a multi-lumen conductor guide 602. FIG. 6A is a schematic transverse cross-sectional view of an exemplary multi-lumen conductor guide 602 of the lead body 502. The multi-lumen conductor guide 602 is an elongated structure that extends along the lead body 502 and that defines a plurality of lumens. The multi-lumen conductor guide 602 defines a stylet lumen 608 configured and arranged to receive a stylet for facilitating insertion of the lead 500 into a patient. The multi-lumen conductor guide 602 also defines a plurality of conductor lumens, such as a conductor lumen 606. The conductor lumens 606 can have any suitable cross-sectional shape, such as round, oval, rectangular, triangular, or the like.

Figure 6B:
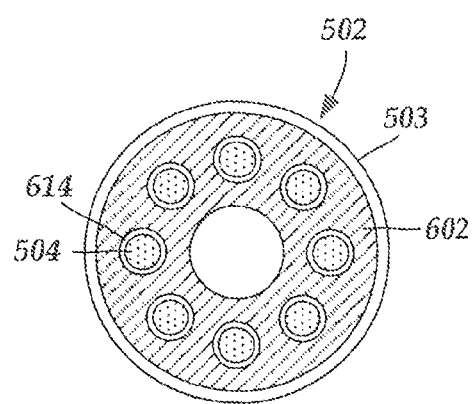
FIG. 6B is a schematic transverse cross-sectional view of one embodiment of conductors disposed in conductor lumens defined in the multi-lumen conductor guide of FIG. 6A, according to the invention.

FIG. 6B is a schematic transverse cross-sectional view of an embodiment of conductors, such as conductors 504, disposed in the conductor lumens 606. Optionally, the conductors 504 include an insulation coating, such as a conductor insulation 614, which is disposed along the circumference of the conductor 504. The conductor insulation 614 is made from any suitable electrically-nonconductive material such as, for example, polyurethane, silicone, or the like. The conductor lumens 606 may be configured to receive any suitable number of conductors including, for example, one, two, three, four, or more conductors 504. In FIGS. 6A-6D, the conductor lumens 606 are each configured and arranged to receive a single conductor 504.

Figure 6C:
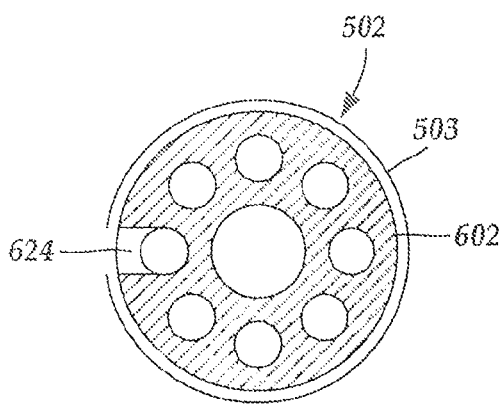
FIG. 6C is a schematic transverse cross-sectional view of one embodiment of the multi-lumen conductor guide of FIG. 6A with a removed portion located between a conductor lumen and an outer surface of the lead body of FIG. 6A, according to the invention.
Figure 6D:
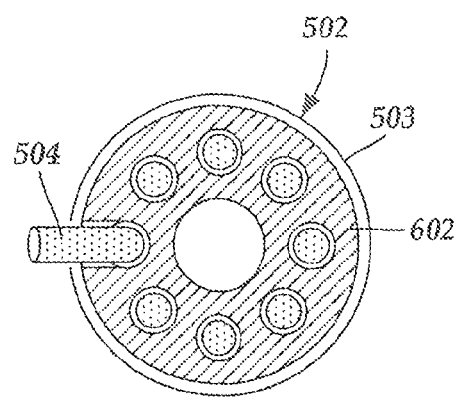
FIG. 6D is a schematic transverse cross-sectional view of one embodiment of the multi-lumen conductor guide of FIG. 6C with a removed portion located between a conductor lumen and an outer surface of the lead body of FIG. 6C, where a conductor extends along the conductor lumen and outward from the removed portion, according to the invention.

As shown in FIG. 6C, the multi-lumen conductor guide 602 may include conductor apertures, such as conductor aperture 624, formed between the conductor lumens 606 and the outer surface 503 of the lead body 502. The conductor apertures 624 provide a passage for the conductors 504 to extend out of the lead body 502 for coupling to the contacts 306 (as shown in FIG. 5). FIG. 6D shows one of the conductors 504 extending through the conductor apertures 624. The conductor apertures 624 may be formed using any suitable technique including, for example, laser ablation, thermal ablation, chemical ablation, drilling, puncturing, boring, or the like.

A multi-lumen conductor guide 602 can be formed of any electrically-nonconductive material suitable for implantation including, but not limited to, polyurethane, silicone, or silicone-polyurethane copolymer. In some embodiments, the multi-lumen conductor guide 602 is formed around the conductors 504 by molding, extrusion, or other methods. In some embodiments, the multi-lumen conductor guide 602 is formed first and then the conductors 504 inserted into the multi-lumen conductor guide 602.

FIGS. 7A-8C illustrate one embodiment of disposing the multi-contact assembly 302 along the lead body 502. FIG. 7A is a schematic transverse cross-sectional view of one embodiment of the multi-contact assembly 302 positioned in proximity to the multi-lumen conductor guide 602. One of the conductors 504 is shown extending outwardly from the multi-lumen conductor guide 602 to the multi-contact assembly 302. In FIG. 7B, one of the conductors 504 is shown extended outwardly from the multi-lumen conductor guide 602 and electrically coupled to the first face 342 of the second contact 306b of the multi-contact assembly 302.

As shown in FIG. 7B, the conductor 504 passes through the conductor aperture 624 of the conductor lumen (606 of FIG. 6A) and couples to the first face 342 of the first contact 306a. The remaining conductors 504 of the lead body 502 may be similarly coupled to the remaining contacts 306 of the multi-contact assembly 302. Once all the conductors 504 are coupled to the contacts 306, the multi-contact assembly 302 can be disposed around a circumference of the lead body 502, as shown by arrows 702, to envelope, or surround, the outer surface 604 of the lead body 502.

In some embodiments, once the multi-contact assembly 302 is disposed around the lead body 502, the first end 332 of the multi-contact assembly 302 can be attached to the second end 334 of the multi-contact assembly 302, thereby coupling the multi-contact assembly 302 to the outer surface 503 of the lead body 502.

FIG. 8A is a schematic transverse cross-sectional view of one embodiment of the multi-contact assembly 302 disposed over the lead body 502. As shown, the multi-contact assembly 302 is wrapped around the outer surface 503 of the lead body 502 such that the first faces 342 of the contacts 306 abut the lead body 502, and the opposing second faces 344 of the electrode 306 is buried beneath the pre-second face 320 of the substrate 304.

In at least some embodiments, the lead body 502 has a circumference that is equal to the width (314 in FIG. 3A) of the multi-contact lead assembly 302. In at least some embodiments, the lead body 502 has a circumference that is equal to widths of the contacts 306. Alternatively, the contacts 306 of the multi-contact lead assembly 302 extended around less than the entire circumference of the lead body 502.

The multi-contact assembly 302 may be coupled to the lead body 502 in any suitable manner. In some embodiments, the first face 318 of the substrate 304 is coupled to the lead body 502, at least in part, by coupling together two opposing interlocking features 352a and 352b. In at least some embodiments, opposing ends of the contacts 306 are coupled together by welding, crimping, soldering, or the like.

In at least some embodiments, adhesive can be employed to couple, at least in part, the first face 318 of the multi-contact lead assembly 302 to the lead body 502. Alternatively or additionally, the multi-contact assembly 302 may be re-flowed to the lead body 502.

Once the multi-contact assembly 302 is coupled to the lead body 502, the pre-second face 320 of the substrate 304 may be ground down to expose the buried second faces 344 of the contacts 306. FIG. 8B is a schematic transverse cross-sectional view of an embodiment of the multi-contact assembly 302 disposed over, and coupled to, the lead body 502. The second face 320 of the substrate 304 of the multi-contact assembly 302 has been ground down to expose the second faces 344 of the contacts 306.

FIG. 8C is a schematic side view of an embodiment of the distal end portion 501 of the lead body 502 with the multi-contact assembly 302 disposed over the lead body 502 and ground down to expose the second faces 344 of the contacts 306. Grinding down the multi-contact assembly 302 to expose the second faces 344 of the contacts 306 may also include grinding down the pre-second face 320 of the substrate 304 to form a second face 820 of the multi-contact assembly 302. In at least some embodiments, the second face 820 of the multi-contact assembly 302 is flush with the second faces 344 of the contacts 306.

Figure 9:
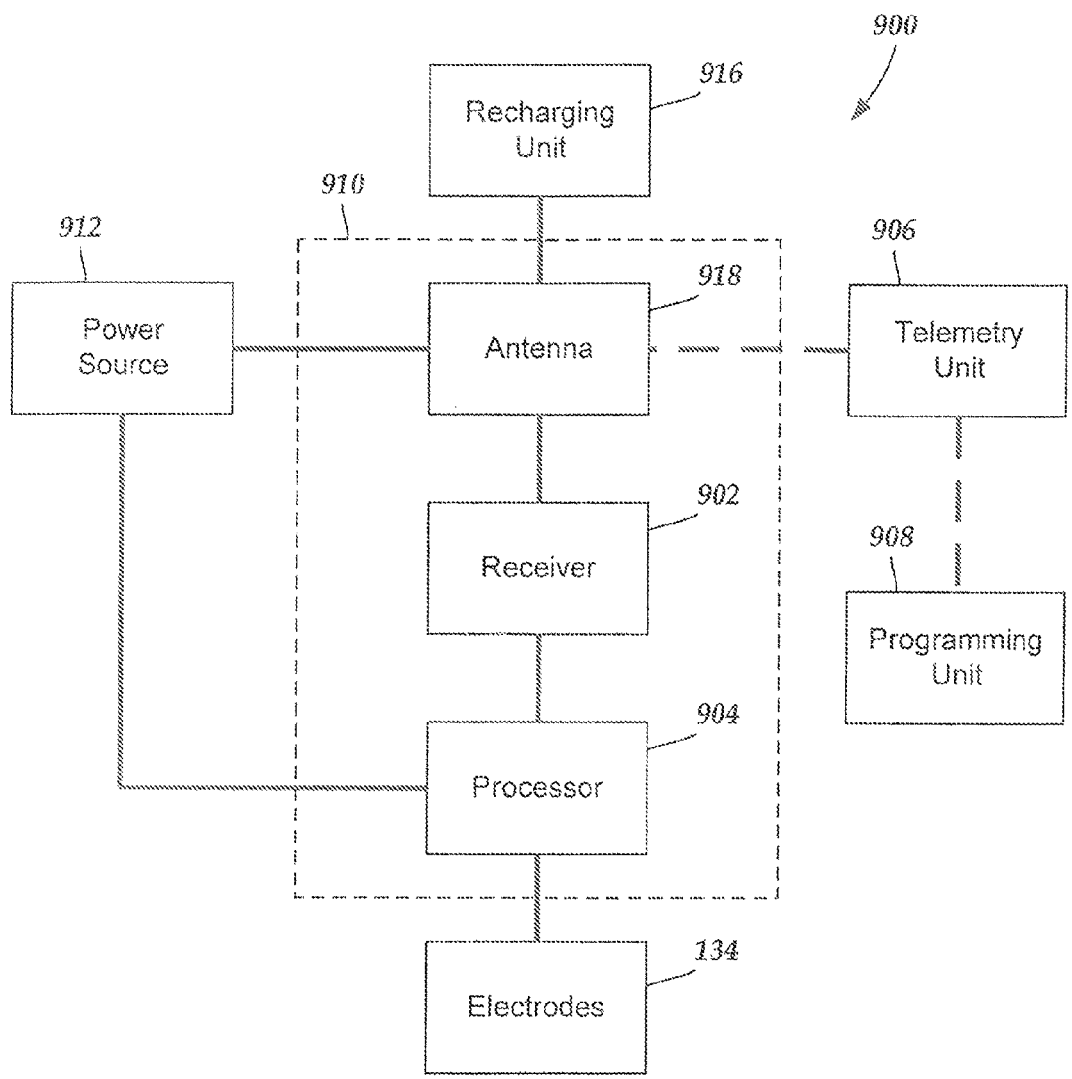
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of forming an electrical stimulation lead, the method comprising:
   molding an electrically-nonconductive substrate over and between a plurality of spaced-apart electrically-conductive contacts to form a multi-contact lead assembly, the substrate having a first face and an opposing second face, the plurality of contacts each having a first face and an opposing second face, wherein the plurality of contacts are disposed along the first face of the substrate with the first face of each of the plurality of contacts exposed along the first face of the substrate and the opposing second face of each of the plurality of contacts covered by material forming the second face of the substrate, wherein the plurality of contacts comprises a first contact and a second contact;
   coupling the multi-contact lead assembly along a first end portion of a lead body with the first face of the substrate conforming to a shape of an outer surface of the lead body and with the multi-contact lead assembly wrapping around the outer surface of the lead body;
   electrically coupling individual conductors extending along a length of the lead body to each of the plurality of contacts of the multi-contact lead assembly; and
   removing at least a portion of the substrate to expose the second faces of the contacts.

2. The method of claim 1, wherein molding an electrically-non-conductive substrate comprises injection molding the electrically-non-conductive substrate over and between the plurality of spaced-apart electrically-conductive contacts.

3. The method of claim 1, wherein coupling the multi-contact lead assembly to a first end portion of a lead body comprises coupling the multi-contact lead assembly to a first end portion of a lead body defining a plurality of conductor lumens.

4. The method of claim 3, wherein coupling the multi-contact lead assembly to a first end portion of a lead body defining a plurality of conductor lumens comprises forming a first aperture through an outer surface of the first end portion of the lead body.

5. The method of claim 4, wherein forming a first aperture through an outer surface of the first end portion of the lead body comprises forming the first aperture between a first conductor lumen of the plurality of conductor lumens and the outer surface of the lead body.

6. The method of claim 5, wherein electrically coupling individual conductors comprises coupling a first conductor of the individual conductors to a first contact of the plurality of contacts of the multi-contact lead assembly, the first conductor extending along the first conductor lumen and extending out of the first conductor lumen through the first aperture.

7. The method of claim 1, wherein the lead body has a circumference that is equal to a width of the multi-contact lead assembly.

8. The method of claim 1, wherein coupling the multi-contact lead assembly to a first end portion of a lead body comprises extending at least one of the plurality of contacts of the multi-contact lead assembly around an entire circumference of the lead body.

9. The method of claim 1, wherein coupling the multi-contact lead assembly to a first end portion of a lead body comprises extending at least one of the plurality of contacts around less than an entire circumference of the lead body.

10. The method of claim 1, wherein molding an electrically-nonconductive substrate comprises molding the electrically-non-conductive substrate over and between a plurality of spaced-apart electrically-conductive electrodes to form a multi-contact lead assembly comprising a plurality of electrodes disposed along the substrate.

11. The method of claim 10, wherein coupling the multi-contact lead assembly to a first end portion of a lead body comprises coupling the multi-contact lead assembly to a distal end portion of the lead body.

12. The method of claim 1, wherein molding an electrically-nonconductive substrate comprises molding the electrically-non-conductive substrate over and between a plurality of spaced-apart electrically-conductive terminals to form a multi-contact lead assembly comprising a plurality of terminals disposed along the substrate.

13. The method of claim 12, wherein coupling the multi-contact lead assembly to a first end portion of a lead body comprises coupling the multi-contact lead assembly to a proximal end portion of the lead body.

14. The method of claim 1 wherein coupling the multi-contact lead assembly to a first end portion of a lead body comprises crimping or welding opposing ends of at least one of the plurality of contacts to one another.

15. The method of claim 1, wherein coupling the multi-contact lead assembly to a first end portion of a lead body comprises using an adhesive to couple the first face of the substrate to the first end portion of the lead body.

16. The method of claim 1, wherein coupling the multi-contact lead assembly to a first end portion of a lead body comprises coupling together interlocking features disposed on opposing end portions of the multi-contact assembly.

17. The method of claim 1, wherein coupling the multi-contact lead assembly to a first end portion of a lead body comprises reflowing material of the multi-contact assembly and the first end portion of the lead body together.

18. The method of claim 1, wherein electrically coupling individual conductors comprises coupling each of the individual conductors to a different first face of each of the plurality of contacts of the multi-contact lead assembly.

19. The method of claim 1, wherein removing at least a portion of the substrate comprises grinding the second face of the substrate of the multi-contact assembly to expose the second face of each of the plurality of contacts through the substrate.

20. The method of claim 1, wherein coupling the multi-contact lead assembly to a first end portion of a lead body comprises wrapping the multi-contact lead assembly around the first end portion of the lead body.

* * * * *